United States Patent
Roa et al.

(10) Patent No.: US 11,350,643 B2
(45) Date of Patent: Jun. 7, 2022

(54) STARCH-BASED TEXTURIZERS FOR LOW PROTEIN YOGURT

(71) Applicant: Corn Products Development, Inc., Westchester, IL (US)

(72) Inventors: Brandon Roa, Bridgewater, NJ (US); Erhan Yildiz, Bridgewater, NJ (US); David Stevenson, Bridgewater, NJ (US); William Anthony, Bridgewater, NJ (US); Jelle Brinksma, Veendam (NL)

(73) Assignee: Corn Products Development, Inc., Westchester, IL (US)

( * ) Notice: Subject to any disclaimer, the term of this patent is extended or adjusted under 35 U.S.C. 154(b) by 193 days.

(21) Appl. No.: 16/464,097

(22) PCT Filed: Nov. 21, 2017

(86) PCT No.: PCT/US2017/062851
§ 371 (c)(1),
(2) Date: May 24, 2019

(87) PCT Pub. No.: WO2018/098181
PCT Pub. Date: May 31, 2018

(65) Prior Publication Data
US 2019/0281849 A1    Sep. 19, 2019

Related U.S. Application Data

(60) Provisional application No. 62/426,944, filed on Nov. 28, 2016.

(51) Int. Cl.
| | | |
|---|---|---|
| *A23C 9/137* | (2006.01) |
| *A23L 29/219* | (2016.01) |
| *C12P 19/14* | (2006.01) |
| *C12P 19/04* | (2006.01) |
| *A23L 29/212* | (2016.01) |
| *A23L 29/30* | (2016.01) |

(52) U.S. Cl.
CPC ............ *A23C 9/137* (2013.01); *A23L 29/212* (2016.08); *A23L 29/219* (2016.08); *A23L 29/35* (2016.08); *C12P 19/04* (2013.01); *C12P 19/14* (2013.01); *A23V 2002/00* (2013.01)

(58) Field of Classification Search
CPC ...... A23C 9/137; A23C 9/1307; A23L 29/212
USPC ................... 426/56, 583, 549, 615
See application file for complete search history.

(56) References Cited

U.S. PATENT DOCUMENTS

| | | |
|---|---|---|
| 5,932,639 A | 8/1999 | Eden et al. |
| 6,054,302 A | 4/2000 | Shi et al. |
| 6,090,594 A | 7/2000 | Kettlitz |
| 6,093,439 A * | 7/2000 | Whaley |
| 6,623,943 B2 | 9/2003 | Schmiedel |
| 6,890,579 B2 | 5/2005 | Buwalda et al. |
| 6,896,915 B2 | 5/2005 | Shi et al. |
| 7,829,600 B1 | 11/2010 | Trksak et al. |
| 2002/0189607 A1 * | 12/2002 | Lavoie et al. |
| 2006/0240148 A1 * | 10/2006 | Nguyen et al. |
| 2013/0236624 A1 * | 9/2013 | Trksak |

FOREIGN PATENT DOCUMENTS

| | | |
|---|---|---|
| EP | 0688872 | 3/1999 |
| EP | 2 014 177 A1 | 1/2009 |
| WO | 200121011 | 3/2001 |

OTHER PUBLICATIONS

Buwalda, P. I., 2014, "Formulating gelaitin free products", pp. 1-5, https://app.knowvel.com/web/view/khtml/print.v/rcid . (Year: 2014).*
McPherson, AE; Jane, J., "Comparison of waxy potato with other root and tuber starches", Carbohydrate Polmers V 40 (1) p. 57-70 (1999).
Cai, Liming; Shi, Yong-Cheng, "Structure and digestibility of crystalline short-chain amylose from debranched waxy wheat, waxy maise, and waxy potato starches", Carbohydrate Polymers v 79(4), p. 1117-1123 (2010).
Cai, Liming; Bai, Yanjie; Shi, Yong-Cheng, "Study on melting and crystallization of short-linear chains from debranched waxy starches by in situ synchrotron wide-angle X-ray diffraction", Journal of Cereal Science v55(3), p. 373-379 (2012).
Cai, Liming; Shi, Yong-Cheng, "Preparation, structure, and digestibility of crystalline A- and B-type aggregates from debranched waxy starches", Carbohydrate Polymers V105, p. 341-350 (2014).

* cited by examiner

*Primary Examiner* — Helen F Heggestad
(74) *Attorney, Agent, or Firm* — Rachael Casey

(57) ABSTRACT

Disclosed herein is at least one low protein yogurt composition comprising at least one dairy ingredient, dairy alternative ingredient, or mixture thereof, and a texturizing agent comprising an inhibited starch and a non-granular, enzymatically-debranched waxy potato starch, wherein said low protein yogurt comprises less than 2.9% dairy protein content, and at least one method for making these low protein yogurt compositions. Also disclosed herein is a texturizing agent comprising an inhibited starch and a non-granular, enzymatically-debranched waxy potato starch.

20 Claims, No Drawings

STARCH-BASED TEXTURIZERS FOR LOW PROTEIN YOGURT

CROSS-REFERENCE TO RELATED APPLICATIONS

This application is a US National Stage under 35 USC § 371 of International Application No. PCT/US2017/062851, filed Nov. 21, 2017, which claims priority to United States Provisional Patent Application Serial No. 62/426,944, filed Nov. 28, 2016, which is hereby incorporated herein by reference in its entirety.

Disclosed herein is one or more low protein yogurt compositions comprising at least one dairy ingredient, dairy alternative ingredient, or mixture thereof, and a texturizing agent comprising an inhibited starch and a non-granular, enzymatically-debranched waxy potato starch, wherein said low protein yogurt comprises less than 2.9% dairy protein content, and one or more method for making these low protein yogurt compositions. Also disclosed herein is a texturizing agent comprising an inhibited starch and a non-granular, enzymatically-debranched waxy potato starch.

Yogurt is a nutritious dairy product which has become quite popular within the last 30 to 40 years. Yogurt is generally produced by culturing one or more dairy ingredients (cream, milk, partially skimmed milk, skim milk or combinations thereof) with a bacterial culture containing the lactic acid producing bacteria including, but not limited to, for example, *Lactobacillus bulgaricus* and *Streptococcus thermophilus*. The dairy ingredient mostly contains fat, protein (primarily casein and whey), lactose, and water. The bacteria convert the lactose to lactic acid, which causes the dairy ingredient to gel, thicken, or gel and thicken and gives yogurt its characteristic tangy taste.

More particularly, the gel structure of a yogurt results from an acid-casein interaction, wherein casein micelles at or near their isoelectric point flocculate, and the colloidal calcium phosphate partially solubilizes as acidity increases. During fermentation of the milk, th pH gradually declines to around 4.5 destabilizing the casein micelles and causing the destabilized micelles to aggregate into a 3-dimensional network in which whey is entrapped. Appearance of whey on the surface ("wheying-off") is due to syneresis.

Yogurts generally fall into one of three styles, namely, Balkan-style or set-style yogurts, Swiss-style or stirred yogurts, and Greek-style or Mediterranean-style (strained) yogurts. Set-style yogurts have a characteristically thick texture and are made by pouring the warm cultured milk mixture into containers and then incubating the mixture without any further stirring. Stirred yogurts are often slightly thinner than set-style yogurts and are made by incubating a warm cultured milk mixture in a vat, cooling the mixture, and then stirring the cooled mixture for a creamy texture, often with fruit, fruit preparations or other flavorings added. Greek-style or Mediterranean yogurt is made by either removing some of the water from the milk or by straining whey from plain yogurt to make it thicker and creamier.

A variety of optional ingredients can be added to yogurt, such as, for example, vitamins (e.g., vitamin A and/or D), sweeteners, flavoring ingredients, color additives and stabilizers (e.g., gelatin, whey protein concentrates ("WPC"), gums (e.g., locust bean gum, guar gum, carrageenan and xanthan), protein, and starch, including modified starch), as well as ingredients to increase the nonfat solids content of the yogurt including but not limited to, for example, concentrated skim milk, nonfat dry milk, buttermilk, whey, lactose, lactalbumins, lactoglobulins and/or other milk solids.

Stabilizers are often added to prevent surface appearance of whey, as well as to improve and maintain body, texture, viscosity and mouthfeel. Examples of stabilizers include gelatin, whey protein concentrates ('WPC'), gums (e.g., locust bean gum, guar gum, carrageenan and xanthan), protein and starch, including modified starch. Yogurts having lower or reduced milk solids have a greater tendency to synerese; therefore, stabilizers are often added to such yogurts. Often a combination of stabilizers is added to the yogurt formulation to avoid defects that may result from the use of just one stabilizer.

Full protein yogurts typically contain about 3.3% to about 3.5% dairy protein (whey and casein) in the starting milk, and around 8.2% dairy solids (protein, lactose, fat, etc.). Due to increasing costs associated with dairy ingredients, manufacturers are constantly looking for more cost effective ways to produce yogurt formulations that exhibit the characteristics consumers have come to expect in yogurt compositions. Further, in many countries, a substantial portion of the population cannot afford the higher cost full protein yogurts described above. Therefore, in order to make these yogurts more affordable, manufacturers often dilute the yogurt with water. However, this dilution is problematic in that, depending upon the degree of dilution, the amount of milk solids is reduced thereby negatively impacting a variety of the characteristics (e.g., viscosity, texture, mouthfeel, etc.) that consumers have come to expect in a yogurt. As noted above, the acid-casein interaction produces the gel structure of yogurt such that adding water to the final yogurt formulation reduces the amount of dairy protein, which destabilizes the gel structure thereby providing a less viscous yogurt.

An additive, such as, powdered milk can be combined with the diluted yogurt formulation to improve, for example, the texture and/or viscosity of the yogurt; however, the use of such additives increases manufacturing costs. Other additives, such as, gums or gelatin can be used to improve the viscosity of the diluted formulation; however, use of these ingredients can result in a yogurt with an unpleasant mouthfeel as well as added cost of manufacture. As a result, there is a need for texturizers and/or viscosifiers that can replace or supplement the dairy protein content of diluted yogurts to provide a low-protein yogurt having comparable organoleptic properties to a full protein yogurt without the high manufacturing costs associated with these full protein yogurts.

In the dairy industry, texturizing agents are often used to compensate for the negative impact that decreased dairy protein content has on the gel-structure of yogurt. Texturizing agents add texture to aqueous food systems that would otherwise have a thin and watery consistency. However, not all texturizing agents are able to adequately compensate for this reduction in dairy protein content.

As mentioned previously, while yogurts with moderate or high levels of dairy protein are well known, there is a demand, particularly in developing countries, for yogurts that have reduced dairy protein levels (and thus reduced cost to manufacture) yet retain the texture characteristics (e.g., viscosity), opacity, and stability (e.g. against syneresis) of full protein products. Accordingly, the yogurt industry needs a texturizing agent that provides low protein yogurt formulations with the texture and appearance consumers have come to expect and that are otherwise lost in yogurt formulations with a reduced dairy protein content.

Provided herein is a low protein yogurt composition comprising at least one dairy ingredient, dairy alternative ingredient, or mixture thereof, and a texturizing agent comprising an inhibited starch and a non-granular, enzymatically-debranched waxy potato starch, wherein said low protein yogurt composition comprises less than 2.9% dairy protein content by weight of the yogurt composition. In another embodiment, the low protein yogurt compositions described herein comprise a dairy protein content of less than or equal to about 1.0, 1.1, 1.2, 1.3, 1.4, 1,5, 1.6, 1.7, 1.8, 1.9, 2.0, 2.1, 2.2, 2,3, 2,4, 2.5, 2,6, 2.7, or 2.8% by weight of the yogurt composition. In yet another embodiment, the low protein yogurt composition contains an effective amount of the texturizing agent to thicken, gel, or thicken and gel the low protein yogurt composition. In still other embodiments, the low protein yogurt compositions described herein contain water. In yet an even further embodiment, the low protein yogurt composition comprises at least one dairy ingredient, dairy alternative ingredient, or mixture thereof, and a texturizing agent comprising an inhibited starch and a non-granular, enzymatically-debranched waxy potato starch, wherein said low protein yogurt composition comprises less than 2.9% dairy protein content by weight of the yogurt composition, with the proviso that said composition does not contain one or more other texturizing agent or with the proviso that said texturizing agent is the sole texturizing agent in the composition.

In one embodiment, the low protein yogurt composition further comprises a gel strength of at least about 1.3 grams, from about 13 grams to about 400 grams, from about 13 grams to about 200 grams, from about 13 grams to about 100 grams, from about 15 grams to about 50 grams, from about 20 grams to about 45 grams, from about 22 grams to about 45 grams, or from about 25 grams to about 42 grams; and wherein said composition comprises an effective amount of said texturizing agent to provide said gel strength. In another embodiment, the gel strength is measured according to the gel strength measurement set forth in Example 1e.

In another embodiment, the low protein yogurt composition further comprises a viscosity of at least about 4000 centipoise, and wherein said texturizing agent is a viscosifier and said composition comprises an effective amount of the texturizing agent to provide the viscosity. In yet another embodiment, the viscosity is measured according to the viscosity measurement set forth in Example 1d. In still another embodiment, the low protein yogurt composition further comprises an opacity of at least about 0.500 A, from about 0.500 A to about 0.850 A, or from about 0.550 A to about 0.800 A, wherein said composition comprises an effective amount of said texturizing agent to provide said opacity. In even yet still another embodiment, the opacity is measured according to the yogurt opacity measurement set forth in Example 1f.

In a further embodiment, the inhibited starch and non-granula, enzymatically-debranched waxy potato starch are present in the texturizing agent in a weight ratio of at least 1.0:1.0, about 3.0:1.0, or about 1.0:1.0 to about 4.0:1.0.

In an even further embodiment, the non-granular, enzymatically debranched. waxy potato starch preferably has a dextrose equivalent (DE) of about 10.0 or less, from about 2.0 to about 9.0, from about 2.5 to about 8.0, from about 3.0 to about 7.0, from about 3.5 to about 5.0, or from about 4.0 to about 5.0, In one embodiment, the non-granular, enzymatically-debranched waxy potato starch has a DE of from about 2.0 to about 9.0, or from about 4.0 to about 5.0. In other embodiments, the non-granular, enzymatically-debranched waxy potato starch is only partially debranched.

In yet even further embodiments, the low protein yogurt composition comprises texturizing agent in an amount of about 10.0% or less, about 0.5% to about 10%, about 0.5% to about 8.0%, about 1.5% to about 7.0%, about 2.0% to about 6.0%, or about 3.0% to about 5.0%, by weight of the composition. In one embodiment, the low protein yogurt composition comprises the texturizing agent in an amount of about 0.5% to about 10% by weight of the composition. In some embodiments, the texturizing agent comprising an inhibited starch and a non-granular, enzymatically-debranched waxy potato starch is the sole texturizing agent in the composition.

Another embodiment is directed to a method of making a low protein yogurt composition comprising less than 2.9% dairy protein content, wherein said method comprises: mixing together at least one dairy ingredient, dairy alternative ingredient, or mixture thereof; a texturizing agent comprising an inhibited starch and a non-granular, enzymatically-debranched waxy potato starch; and optionally, water to form a yogurt base; and culturing the yogurt base, wherein said texturizing agent is present in an effective amount to thicken, gel, or thicken and gel the low protein yogurt composition.

Another embodiment is directed to a texturizing agent comprising an inhibited starch and a non-granular, enzymatically-debranched waxy potato starch, wherein the weight ratio of the inhibited starch to the non-granular, enzymatically-debranched waxy potato starch is at least 1.0:1.0, about 3.0:1.0, or from about 1.0:1.0 to about 4.0:1.0, and wherein the non-granular, enzymatically-debranched waxy potato starch has a DE of about 10.0 or less, from about 2.0 to about 9.0, from about 2.5 to about 8.0, from about 3.0 to about 7.0, from about 3.5 to about 5.0, or from about 4.0 to about 5.0.

In contrast to full-protein yogurts, the yogurt described herein is a yogurt composition comprising a reduced dairy protein content. One embodiment is directed to one or more low protein yogurt compositions comprising at least one dairy ingredient, dairy alternative ingredient, or mixture thereof, and a texturizing agent comprising an inhibited starch and a non-granular, enzymatically-debranched waxy potato starch, wherein said low protein yogurt composition comprises a dairy protein content of less than 2.9% or less than or equal to about 1.0, 1.2, 1.3, 1.4, 1.5, 1.6, 1.7, 1.8, 1.9, 2.0, 2.1, 2.2, 2.3, 2.4, 2.5, 2.6, 2.7, or 2.8% by weight of the yogurt composition. Another embodiment is directed to one or more low protein yogurt compositions comprising water; at least one dairy ingredient, dairy alternative ingredient, or mixture thereof; and a texturizing agent comprising an inhibited starch and a non-granular, enzymatically-debranched waxy potato starch, wherein said low protein yogurt composition comprises a dairy protein content of less than 2.9% or less than or equal to about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, or 2.8% by weight of the yogurt composition. In yet another embodiment, the texturizing agent described herein provides a low protein yogurt with texture and appearance characteristics (e.g., opacity) similar or equivalent to a full protein yogurt.

The term "yogurt" refers to an acidified food product containing a dairy ingredient, dairy alternative ingredient, or mixture thereof, and having a gelled texture. Thus, the term yogurt includes acidified food products that meet a standard of identity for yogurt, as well as acidified food products that do not meet such a standard.

While full protein yogurts typically contain about 3.3% to about 3.5% dairy protein, the phrase "full protein yogurt" refers to a yogurt composition having a dairy protein content of 2.9% or more by weight of the yogurt composition. Accordingly, the phrase "low protein yogurt" refers to a yogurt having a dairy protein content of less than 2.9% or less than or equal to about 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, or 1.0% by weight of the yogurt composition. In another embodiment, the low protein yogurt composition described herein comprises less than 2.9% dairy protein by weight of the composition. In an even still further embodiment, the low protein yogurt composition described herein comprises about 2.0% or less dairy protein by weight of the composition. In still other embodiments, low protein yogurt composition described herein comprises about 1.0% dairy protein or less by weight of the composition.

The phrase "dairy ingredient" refers to one or more food products containing milk or one or more food products derived from milk.

The phrase "dairy alternative ingredient" refers to one or more food product derived from grain, seed, or plant sources (e.g., rice milk, soy milk, hemp milk, coconut milk, almond milk, pulse milk (e.g., pea milk), and peanut milk).

The phrases "Waxy starch" or "low amylose starch" refer to a starch or flour having about 10% or less amylose by weight of the starch granule. In one embodiment, the waxy starch contains about 5% or less amylose, about 2% or less amylose, or about 1% or less amylose by weight of the starch granule. In another embodiment, the waxy starch contains an amylopectin content of at least about 90%, at least about 95%, at least about 97%, or at least about 99%, amylopectin by weight of the starch granule.

In one embodiment, the components of the texturizing agent described herein (i.e., the inhibited starch and non-granular, enzymatically-debranched waxy potato starch) are pre-blended prior to incorporation into the yogurt compositions described herein. In another embodiment, the components of the texturizing agent described herein (i.e., the inhibited starch and non-granular, enzymatically-debranched waxy potato starch) are each added separately to the yogurt compositions described herein (i.e.., are not pre-blended prior to being added).

In one embodiment, the inhibited starch has substantial native granule integrity and has been inhibited so that under the processing conditions of preparing a yogurt composition described herein the starch will substantially retain granule integrity. In another embodiment, the predominant granule integrity of the starch is not destroyed, and will most likely be swollen and exhibit a reduced degree of crystallinity, if any. In still another embodiment, the starch retains at least part of its granular structure, thereby exhibiting at least some intact starch granules, although some granule fragmentation is acceptable and typical to processes involving homogenizers or other high shear processing. Such fragmentation can occur in larger inhibited starch granules such as potato starch during product processing (e.g., homogenization), yet the inhibited starch fragments can still provide a viscosifying effect in the end product.

In yet another embodiment, the inhibited starch described herein is derived from a native starch found in nature. In another embodiment, the native source from which the inhibited starch is derived is selected from a cereal, e.g., wheat, corn or maize, rice, and oat; tubers and roots, e.g., potato and tapioca; legumes; and fruits. In another embodiment, the inhibited starch described herein is derived from a plant obtained by standard breeding techniques, including, but not limited to, for example, crossbreeding, translocation, inversion, transformation, insertion, irradiation, chemical or other induced mutation, or any other method of gene or chromosome engineering to include variations thereof. In addition, inhibited granular waxy starch derived from a plant grown from induced mutations and variations of the above generic composition that can be produced by known standard methods of mutation breeding are also suitable herein. It is understood that the source of the enzymatically-debranched waxy potato starch can also be obtained by these techniques.

In one embodiment, the inhibited starch is any starch variety, including low amylase (waxy) varieties. In another embodiment, the starch variety is selected from corn, rice, tapioca, cassava, potato, wheat, waxy corn, waxy potato, waxy sweet potato, waxy barley, waxy wheat, waxy rice, waxy sago, waxy amaranth, waxy tapioca, waxy arrowroot, waxy canna, waxy pea, waxy banana, waxy oat, waxy rye, waxy triticale, and waxy sorghum.

Inhibition of the starch used in low protein yogurt compositions described herein can be accomplished by a variety of known methods. Inhibition includes both chemical and physical (thermal) inhibition. In one embodiment, the inhibited starch is a thermally inhibited starch. As used herein, the phrase "thermally inhibited starch" means a starch subjected to a heat treatment process that results in the starch becoming and remaining inhibited.

In one embodiment, the starch granule is inhibited by chemically crosslinking the granule with a food grade crosslinking reagent. Such crosslinking toughens the granule so that on swelling, the integrity of the swollen granule is maintained.. Useful crosslinking reagents include a phosphate-based crosslinking reagent, such as, for example, a soluble metaphosphate (e.g., sodium trimetaphosphate (hereinafter STMP); phosphorous oxychloride (hereinafter $POCl_3$)); and linear dicarboxylic acid anhydrides. In one embodiment, the crosslinking reagent is $POCl_3$, STMP or adipic-acetic anhydride. The crosslinked starch can be further modified by, for example, derivatization. Crosslinking can be conducted using methods known in the art. The amount of crosslinking can vary depending upon the desired viscosity. In one embodiment, the inhibited starch is moderately to highly crosslinked. The specific conditions employed in crosslinking depend upon the type of crosslinking agent used, the type of base starch employed, the reaction scale utilized, and so forth.

It will be appreciated by one of ordinary skill in the art that an increased level of crosslinking is generally obtained by use of increased amounts of crosslinking reagent. However, others factors such as length of time of reaction (longer time promotes crosslinking), pH of reaction medium (higher pH promotes crosslinking), and conditions of drying (longer time and/or higher drying temperatures promote crosslinking) will also affect the degree of crosslinking, and thus, degree of inhibition, except when the reaction medium is neutralized or made mildly acidic (e.g., pH of 5 to 6), or the product starch is washed to a neutral pH before drying.

When the crosslinking agent utilized is $POCl_3$, the degree of crosslinking is at least about 0.01%, at least about 0.02%, from about 0.01% to about 0.08%, from about 0.02% to about 0.05%, or from about 0.03% to about 0.045% by weight of phosphorus oxychloride reagent used to cross-link the starch. Weight percentages are by weight of the starch. The use of other crosslinking agents should be in amounts sufficient to provide equivalent levels of crosslinking.

Starch inhibition can be characterized by Brabender curves. For a highly inhibited starch, the Brabender curve will be flat, indicating that the starch is so inhibited it is resisting any further gelatinization, or the curve will be a rising Brabender curve, indicating that gelatinization is occurring at a slow rate and to a limited extent. For a less inhibited starch, the Brabender curve will be a dropping curve, but the overall breakdown in viscosity from the peak viscosity will be lower than that for a non-inhibited starch.

The inhibited starch can optionally be further treated by a combination of modifications in any order, provided the modification does not destroy the granular nature of the starch. Such additional modifications include, e.g., without limitation, stabilization, acetylation, esterification, hydroxyethylation, hydroxypropylation, phosphorylation, cationic modification, anionic modification, and so forth. Base starches suitable for subsequent modification also optionally include starches prepared by oxidation, enzyme conversion, acid hydrolysis, heat and/or acid dextrinization, thermal and/or sheared starches.

In one embodiment, the inhibited starch is further modified to obtain extended shelf-life in the low protein yogurt; that is, the starch is stabilized. The starch can be stabilized by any of a variety of means, including substitution with STPP, succinic anhydride, acetyl or hydroxypropyl groups. Acetylation adds acetyl groups to the crosslinked starch, thereby inhibiting syneresis of the low protein yogurt composition described herein. Stabilization of the starch can occur after crosslinking by making the pH of the reaction slurry mildly alkaline and then adding the stabilizing agent (e.g., acetic anhydride). In one embodiment, the stabilizing agent is added to the reaction slurry in an amount of from about 0.5% to about 10.0%, from about 0.75% to about 8.0%, or from about 1.0% to about 7.0% by weight of the starch granule.

In one embodiment, the inhibited starch is a food quality starch in which the starch is modified by both crosslinking and stabilization. In another embodiment, the inhibited starch is a stabilized and cross-linked starch selected from hydroxypropylated distarch phosphate, acetylated distarch adipate, and waxy maize starches having at least one recessive sugary-2 allele that is subsequently chemically cross-linked or thermally inhibited.

In one embodiment, the inhibited starch is a hydroxypropylated distarch phosphate with a degree of substitution of from about 3.5% to about 8.8% or from about 5.7% to about 6.7% by weight of the bound propylene oxide on starch. In another embodiment, the degree of cross-linking is at least about 0.01%, from about 0.01% to about 0.08%, from about 0.02% to about 0.05%, or from about 0.03% to about 0.045% by weight of phosphorus oxychloride reagent used to crosslink the starch. Weight percent is based on weight of the starch. As used herein, food quality starches are starches that are edible by animals, including human beings.

The enzymatically-debranched waxy potato starch can be prepared by the following process. A starch suspension or slurry is prepared from native waxy potato starch and water in a concentration of about 5% to about 50% starch solids by weight of the slurry. This suspension or slurry is gelatinized by heating (e.g., by jet-cooking) and then cooled. The pH of this cooled suspension is adjusted depending upon the requirements of the enzyme chosen to debranch the starch to a pH of from about 3.0 to about 7.5. This pH-adjusted suspension is then mixed with a debranching enzyme (e.g., isoamylase pullulanase EC. 3.2.1.41 and/or other debranching enzymes) and heated to a temperature suitable for the chosen debranching enzyme (typically from about 25° C. to about 75° C., more typically about 60° C. +/−2° C.). The mixture is stirred until the desired degree of debranching is obtained, and the suspension then heated to inactivate the debranching enzyme(s) (e.g., to about 130° C. to about 150° C.). Typical debranching parameters include addition of the debranching enzyme in an amount of from about 0.01% to about 5.00%, from about 0.05% to about 2.00%, or from about 0.10% to about 0.75% by weight of anhydrous starch added to the reaction mixture, and a debranching period of from about 3.5 hours to about 25.0 hours or from about 10.0 hours to about 20.0 hours. These debranching parameters are ultimately dependent upon enzyme dosage concentration and the desired amount of debranching. Optionally, the starch can be isolated by drying (e.g., by spray-drying).

As noted above, the enzymatically-debranched waxy potato starch described herein is prepared using a debranching enzyme. In one embodiment, the debranching enzyme rapidly hydrolyzes only the α-1,6-D-glucosidic bonds, releasing short chain amylose. In another embodiment, the debranching enzyme is an α-1,6-D-glucanohydrolase. In still another embodiment, the α-1,6-D-glucanohydrolase is an isoamylase EC.3,2.1.68, pullulanase EC. 3.2.1.41, or combination thereof. In still yet another embodiment, the α-1,6-D-glucanohydrolase enzyme is an endo-enzyme capable of hydrolyzing the α-1,6-D-glucosidic linkages of the starch molecule, and incapable of any significant degree of hydrolysis of the α-1,4-D-glucosidic bonds.

In one embodiment, the enzymatically-debranched waxy potato starch is incompletely or only partially debranched and, thus, contains amylopectin, which has residual branching. For example, depending on the end use and the starch source selected, the starch may be debranched by treatment with an alpha-1,6-D-glucanohydrolase until up to 65%, by weight, of the starch has been debranched to short chain amylose. In another embodiment, the enzymatically-debranched waxy potato starch contains up to 65%, by weight, short chain amylose. The degree of debranching of the debranched waxy potato starch is determined by its dextrose equivalent ("DE"), which is a measure of the amount of reducing sugars present in a sugar product, relative to dextrose, expressed as a percentage on a dry basis. A higher degree of debranching is typically indicated by a higher DE. In one embodiment, the DE of the enzymatically-debranched waxy potato starch is about 10.0 or less, from about 2.0 to about 9.0, from about 2.5 to about 8.0, from about 3.0 to about 7.0, from about 3.5 to about 5.0, or from about 4.0 to about 5.0. In another embodiment, the DE of the enzymatically-debranched waxy potato starch is about 10.0 or less, from about 2.0 to about 9.0, from about 3.5 to about 5.0, or from about 4.0 to about 5.0. In still another embodiment, the DE of the enzymatically-debranched waxy potato starch is from about 3.5 to about 5.0 or from about 4.0 to about 5.0. In yet still another embodiment, the DE of the enzymatically-debranched waxy potato starch is about 10.0 or less or from about 4.0 to about 5.0. In one embodiment, the DE is determined as set forth in Example 1b.

In one embodiment, a good correlation exists between the DE of the enzymatically-debranched waxy potato starch and the gel strength exhibited by gels of such starch in a model aqueous system as well as in food formulations. The model aqueous system can simply be an aqueous dispersion of the enzymatically-debranched waxy potato starch in water at 8% to 10% solids by weight. Thus, DE is an excellent indicator of which enzymatically-debranched. waxy potato starches will provide the strongest gels.

In one embodiment, the texturizing agent described herein comprises an inhibited starch and a non-granular, enzymatically-debranched waxy potato starch in a weight ratio of inhibited starch to non-granular enzymatically-debranched waxy potato starch of from about 1.0:1.0 to about 19.0:1.0, from about 13.0:7.0 to about 9.0:1.0, or from about 3.0:1.0 to about 17.0:3.0. In another embodiment, the inhibited starch and non-granular, enzymatically-debranched waxy potato starch are present in the texturizing agent in a weight ratio of about 1.0:1.0 to about 4.0:1.0. In still another embodiment, the inhibited starch and non-granular, enzymatically-debranched waxy potato starch are present in the texturizing agent in a weight ratio of about 3.0:1.0. In yet still another embodiment, the low protein yogurt composition described herein comprises the texturizing agent described herein in an amount of about 10.0% or less by weight of the composition. In still another embodiment, the low protein yogurt composition described herein comprises the texturizing agent described herein in an amount of about 0.5% to about 10.0%, about 1.5% to about 7.0%, or about 2.0% to about 6.0% by weight, of the composition.

Yogurt compositions vary in different countries and in different localities and markets within each country. In formulating yogurts, consideration must be given to legal requirements, quality of product desired, raw materials available, plant equipment and processes, trade demands, competition and costs.

In general, yogurt comprises a cultured milk product produced by culturing at least one dairy ingredient that is combined to form a yogurt base with a characterizing bacterial culture. The bacterial culture typically contains *Lactobacillus bulgaricus* and *Streptococcus thermophilus*. The culture may optionally comprise additional culture specie(s) as is known in the art, such as, for example, *Lactobacillus acidophilus* and/or bifidus. Alternatively, dairy ingredients can be directly acidified, for example, to a pH of from about 3.5 to about 5.0 or about pH 4.1 to about pH. 4.7.

Stabilizers are available that provide the viscosity needed in a yogurt having 2.9% or more dairy protein. At least one texturizing agent described herein addresses the need for a stabilizer or texturizer that gives yogurt compositions having 2.9% or less or less than or equal to about 2.8, 2.7, 2.6, 2.5, 2.4, 2.3 2.2, 2.1, 2.0, 1.9, 1.8, 1.7, 1.6, 1.5, 1.4, 1.3, 1.2,1.1, or 1.0% dairy protein content (based on weight of the composition) comparable viscosity, mouthfeel, and opacity to a full protein yogurt at a cost that is lower than the cost to manufacture a full protein yogurt. In another embodiment, at least one texturizing agent described herein finds use in a yogurt composition comprising about 2.5% dairy protein or less based on weight of the composition. In a still further embodiment, at least one texturizing agent described herein finds use in a yogurt composition comprising about 2.0% dairy protein or less based on weight of the composition. In a yet still further embodiment, at least one texturizing agent described herein finds use in a yogurt composition comprising substantially 0% dairy protein, such as, for example, yogurts prepared, for example, from a nondairy milk source, such as, e.g., almond milk and soy milk.

In one embodiment, the low protein yogurt composition described herein is selected from a set-style yogurt, stirred yogurt, and strained yogurt. In another embodiment, the low protein yogurt composition described herein is set-style yogurt or a stirred yogurt.

Low protein yogurt compositions are generally formulated and manufactured in a manner similar to full protein yogurt compositions with the exception that they are further diluted with water in order to reduce their cost of manufacture. In one embodiment, the water is added in an amount of about 10.0% to about 12.0% by weight of the yogurt composition in order to dilute the composition, resulting in a total water content of at least about 70.0% by weight of the low protein yogurt composition. The addition of water to the formulation reduces the overall dairy protein content of the yogurt composition, thereby negatively affecting the properties of the low protein yogurt composition.

In order to obtain a low protein yogurt composition having textural and viscosity characteristics similar to a full protein yogurt composition, said low protein yogurt composition comprises added water (i,e,, water in addition to that normally present in the dairy ingredient, dairy alternative ingredient, or mixture thereof); at least one dairy ingredient, dairy alternative ingredient, or mixture thereof; a texturizing agent comprising at least an inhibited starch and an enzymatically debranched waxy potato starch; and, optionally, other ingredients, such as, for example, sweeteners and/or flavoring agents. Further, the at least one dairy ingredient, dairy alternative ingredient, or mixture thereof is selected to provide a full fat, low fat, or no fat yogurt composition. In one embodiment, the yogurt base, before addition of bulky flavors and/or sweeteners, comprises about 0.1% to about 4% milkfat and at least about 1% or 8.25% milk-solids-not-fat ("MSNF"), and a titratable acidity of at least about 0.9%, expressed as lactic acid.

In another embodiment, the low protein yogurt composition described herein comprises a viscosity of at least about 4000 centipoise ("cP"). In yet a further embodiment, the texturizing agent is a viscosifier and the low protein yogurt composition described herein comprises an effective amount of the texturizing agent to provide a viscosity of at least about 4000 cP. In an even still further embodiment, the low protein yogurt composition described herein comprises a viscosifying amount of the texturizing agent described herein in an effective amount to impart a viscosity of at least about 4000 cP to the yogurt composition, optionally, after seven weeks storage. In another embodiment, the low protein yogurt composition described herein comprises an effective amount of the texturizing agent described herein to impart a viscosity of from about 4000 cP to about 6200 cP to the composition, optionally, after seven weeks.

In some embodiments, the low protein yogurt composition described herein comprises the texturizing agent described herein in an amount of about 10% or less or from about 0.5% to about 10% by weight of the composition. In other embodiments, the low protein yogurt composition comprises the texturizing agent described herein in an amount of from about 0.5% to about 8.0%, about 1.5% to about 7.0%, about 2.0% to about 6.0%, or about 3.0% to about 5.0%, by weight of the composition.

In one embodiment, the weight ratio of the inhibited starch ("IS") to the enzymatically debranched waxy potato starch ("EDWP") in the texturizing agent is at least 1.0:1.0. In some enibodiments, the IS and EDWP are present in a ratio of about 3.0:1.0. In other embodiments, the IS and EDWP are present in a ratio of about 1.0:1..0 to about 4.0:1.0.

In another embodiment, at least ono low protein yogurt composition described herein comprises an effective amount of the texturizing agent described herein to impart a soft gelled texture to said composition. Gelling can be measured by the gel strength test, described below. As used herein, a yogurt "gels" when it exhibits gel strength of at least about 1.3 grams in the gel strength measurement method described below. "Gel strength" refers to the gel strength that is measured prior to any heating of the gel that is sufficient to melt the enzymatically-debranched waxy potato starch. In some embodiments, the gel strength of the low protein yogurt composition described herein is at least about 13 grams, from about 13 grams to about 400 grams, from about 13 grams to about 200 grams, from about 13 grams to about 100 grams, from about 15 grams to about 50 grams, from about 20 grams to about 45 grams, or about 22 grams to about 45 grams. In other embodiments, the gel strength of the low protein yogurt composition described herein is from about 25 grams to about 42 grams.

In one embodiment, at least one low protein yogurt composition comprising a texturizing agent comprising an inhibited starch and a non-granular, enzymatically-debranched waxy potato starch has improved opacity compared to a low protein yogurt composition that does not contain said texturizing agent. In another embodiment, a texturizing agent comprising an inhibited starch and a non-granular, enzymatically-debranched waxy potato starch restores at least about 10%, at least about 20%, at least about 30%, or from about 35% to about 60% of the opacity that is lost in a non-fat yogurt that does not contain the texturizing agent and has a dairy protein content that is reduced from 2.9% to 1%. In some embodiments, the low protein yogurt compositions described herein have an opacity of at least about 0.500 A, from about 0.500 A to about 0.850 A, or from about 0.550 A to about 0.800 A, as measured by the test described in Example 1f below.

In one embodiment, the at least one low protein yogurt composition described herein contains a texturizing agent comprising an inhibited starch and a non-granular, enzymatically-debranched waxy potato starch described herein as the sole viscosifying agent (other than any dairy protein that may be present). In another embodiment, the at least one low protein yogurt composition described herein further comprises an optional stabilizer. In yet another embodiment, the optional stabilizer is selected from gelatin, gum acacia, carrageenan, gum karaya, pectin, gum tragacanth, xanthan, maltodextrins, and mixtures thereof. The type and level of optional stabilizer depends on the filling viscosity range for the yogurt as described in detail below. The optional stabilizers are well known food ingredients and are commercially available, In one embodiment, at least one low protein yogurt composition described herein is stabilized, e.g., against syneresis for an extended period of refrigerated storage, typically for at least about seven weeks of storage at refrigerated temperatures, e,g., 4° C. Stabilization can be achieved by the type of starch used or by modifying the degree of stabilization of the starch.

In other embodiments, at least one low protein yogurt composition described herein optionally comprises at least one nutritive carbohydrate sweetening agents. Exemplary useful nutritive carbohydrate sweetening agents include, but are not limited to, sucrose; high fructose corn syrup; dextrose; various DE corn syrups; beet or cane sugar; invert sugar (in paste or syrup form); brown sugar; refiner's syrup; molasses (other than blackstrap); fructose; fructose syrup; maltose; maltose syrup; dried maltose syrup; malt extract; dried malt extract; malt syrup; dried malt syrup; honey; maple sugar; and mixtures thereof.

In other embodiments, at least one low protein yogurt composition described herein is prepared by adding—typically pre-blended—the various dry ingredients to the wet ingredients, and blending them together to form the yogurt base. This yogurt base can then optionally be deaerated and homogenized. After blending, deaerating, heating and homogenizing, the low protein yogurt composition is pasteurized and then rapidly cooled to a temperature of about 40° C. to about 50° C. Once cooled, the pasteurized low protein yogurt composition is cultured. This culturing step can include the two sub-steps of inoculation—or adding a live yogurt culture to form an inoculated yogurt base—and then fermenting or incubating the inoculated yogurt base, wherein about 0.02% to about 0.06% or about 0.02% to about 0.05% of yogurt culture is added. The inoculated low protein yogurt composition is then incubated to allow the live yogurt culture to ferment and form the yogurt. The incubation period for yogurt ranges from about 3 to about 10 hours at temperatures of about 38° C. to about 46° C. (about 100° F. to about 115° F.). Fermentation progress is monitored by pH measurements at regular intervals until the desired acidity level is obtained, typically at a pH of about 3.5 to about 5.0 or from about 4.1 to 4.7. Acid development and bacterial growth are then arrested by cooling the mixture, generally to a filling temperature of about 21° C. (70° F.) or less, about 3° C. to about 16° C. (about 38° F. to about 60° F.), or about 45° C. (about 40° F.). As an alternative to culturing, the low protein yogurt composition can be directly acidified by addition of a food grade acid, typically to a pH of from about 4.1 to about 4.7. Exemplary food grade acids include, but are not limited to, lactic acid, citric acid, malic acid, gamma delta lactone, tartaric acid, acetic acid, any other food grade acid, and combinations thereof.

After incubating, the low protein yogurt composition is typically mixed/sheared to form a stirred style yogurt. Mixing can be performed either partially or fully, either before or after the cooling arrest step. Mixing blends the low protein yogurt composition to impart a smooth texture and mouthfeel to the yogurt body. This mixing step can also optionally include the addition of a high potency sweetener, e.g., aspartame, acesulfame K, sucralose, saccharine, cyclamate, or mixtures thereof (in their soluble salt forms) to the composition.

In an optional embodiment, the cooled low protein yogurt composition can be further blended (i.e., without resting) with additives, such as, for example, fruit and/or fruit puree; colorants; flavorants; high potency sweeteners, e.g., aspartame, acesulfame, sucralose, saccharine, cyclamate and mixtures thereof (in their soluble salt forms); vitamins; and minerals, especially calcium salts (e.g., tricalcium phosphate and/or other dispersible calcium salts). Alternatively, fruit and/or fruit puree or preserves can be added to a container before addition of the yogurt when preparing a product having fruit on the bottom. When sweeteners are added, a good balance in desired sweetness versus yogurt growth inhibitory effects is obtained when the sweetener is added in an amount of about 6.0% to about 12.0% by weight based on weight of the low protein yogurt composition.

In some embodiments, the stirred style low protein yogurt composition further comprises fruit preserves dispersed throughout the yogurt phase, wherein said fruit preserves are about 0.1% to about 25.0% by weight of the composition. The term "yogurt phase" refers to the yogurt alone (i.e., with non-fruit additives dispersed or dissolved in the yogurt) or the yogurt with other additives mixed with fruit puree.

In some embodiments, at least one low protein yogurt composition described herein is nonfat, wherein said nonfat low protein yogurt comprises less than about 0.5% fat. In other embodiments, at least one low protein yogurt composition described herein is low fat, wherein said low fat low protein yogurt comprises about 1.5% fat. In still other embodiments, at least one low protein yogurt composition described herein is reduced fat, wherein said reduced fat low protein yogurt has about 2% fat. In even further embodiments, at least one low protein yogurt composition described herein is full fat, wherein said full fat low protein yogurt has about 3.5% fat. The yogurt composition can thus be prepared with a variety of dairy ingredients (e.g., whole milk, partially skimmed milk, skim milk, and/or nonfat dry milk), dairy alternative ingredients (e.g., rice milk, soy milk, hemp milk, coconut milk, almond milk, pulse milk (e.g., pea milk), and peanut milk), or mixtures thereof.

In another embodiment, at least one low protein yogurt composition described herein optionally comprises other milk fraction ingredients, such as, for example, buttermilk, whey, milk protein, lactose, lactalbumins, and lactoglobulins. In some embodiments, lactose is removed and/or minerals are added.

In some embodiments, at least one low protein yogurt composition described herein comprises whey permeate. Whey permeate is a by-product of cheese making and is produced when whey is filtered to remove most of the residual protein. Whey permeate is typically comprised of water, lactose, and minerals, as well as small amounts (i.e., less than about 1% by wt. each) of residual milk protein, fat, and flavor compounds. The addition of whey permeate to a low protein yogurt formulation can restore some of the flavor and mouthfeel that is lost when the protein levels are reduced. In some embodiments, whey permeate is added to at least one low protein yogurt composition described herein in an amount of from about 0.5 wt. % to about 5.0 wt. % or from about 1.0 wt. % to about 3.5 wt. % by weight of the composition. The weight ratio of the texturizing agent described herein to whey permeate in the at least one low protein yogurt composition described herein is from about 1.25:1.13 to about 2.5:1.0 or from about 1.5:1.0 to about 2.0:1.0.

The resultant low protein yogurt composition is stored at conventional refrigerator temperatures, generally at a temperature of about 0° C. to about 15° C., and typically about 0° C. to about 5° C.

EXAMPLES

The yogurt compositions disclosed herein are described in more detail in the following non-limiting examples. All amounts, parts and percentages in the specification and claims are by weight, unless noted otherwise.

Methods and Materials 1.a. Production of Enzymatically-Debranched Waxy Potato Starch A starch slurry for the enzymatic reaction was prepared by suspending 1.5 kg of waxy potato starch (ELIANE™ 100 waxy potato starch, available from Avebe, Veendam. The Netherlands) in 6 kg of tap water. This suspension was pre-acidified to a pH of 4.0 to 4.1 with aqueous hydrochloric acid and then jet-cooked at approximately 155-160° C. The solution was transferred directly into a double walled reactor heated to 58.5° C. and then pH adjusted, if necessary, to a pH of 4.6 using aqueous hydrochloric acid (1M). A debranching enzyme (PROMOZYME® D2 pullulanase, available from Novozymes A/S, Bagsvaerd, Denmark) was added at various wt. % concentrations (see Table 1), based on the anhydrous weight of the starch (15% starch solids), to the reaction mixture. After stirring at 100 rpm for various time periods, the enzyme was deactivated by jet cooking at greater than 140° C. The reaction mixture was then diluted with tap water and spray dried (250° C. inlet; 110° C. outlet), providing enzymatically-debranched waxy potato starch having a typical moisture content of about 6%.

1b. Determination of Dextrose Equivalence (Luff Schoorl Method)

Dextrose Equivalence ("DE") was determined based on the Luff Schoorl method as set forth in "ISI 24-1e Determination of Reducing Sugar, DE by Luff-Schoorl's Method". International Starch Institute, Science Park Aarhus, Denmark, Rev.: LT 22.01.2002.

This method is based upon iodine titration of excess copper. More specifically, 0.5-1.0 g of enzymatically-debranched waxy potato ("EDWP") starch (as dry starch), 25.0 ml Luff-Schoorl reagent (available from Fischer Scientific), and 10 ml of demiwater are mixed together in flask and allowed to boil for 10 min from the point when the mixture begins boiling. The mixture is then cooled down by placing the flask in a waterbath for about 0.5 hrs. After cooling, 10 ml of potassium iodide (KI) solution and 25 ml of sulfuric acid $H_2SO_4$) are added to the mixture and the mixture is titrated with sodium thiosulphate to a white solution.

The DE is calculated via the following equation: (e factor×100)/((100-moisture of the EDWP starch)×sample amount×1000). The e factor of the titrate for the used amount of sodium thiosulphate is determined by subtracting the used titrate from the blank (i.e. Blank-titrate). The blank is determined by repeating the above described titration process without adding the EDWP starch thereto. That is, the titration process excludes the addition of the EDINT starch to provide the blank.

1c. Method of Preparing Stirred Yogurt

Stirred yogurt samples were prepared in the following manner. The dry ingredients were blended together and added to at least one dairy ingredient and water and mixed together in a Breddo Likwifier blender (available from Breddo Likwifier, a Division of Caravan Ingredients Co., Kansas City, Mo., USA) for 15 minutes at 500 RPM. This mixture was transferred to a holding/feed tank equipped with a Lightnin Mixer (available from SPC Corporation, Rochester, N.Y., USA) for constant agitation while feeding into a MicroThermics® Model 25-2S High-Temperature Short-Time processing equipment (available from Micro-Thermics. Inc., Raleigh, N.C., USA). In the upstream process, the mixture was homogenized at 65° C. and 120/35 Bar (1st/2nd stage) using a dual stage homogenizer (available from GEA Niro Soavi North America, Bedford, N.H., USA), and then pasteurized at 95° C. for 6 minutes. The mixture was then cooled to an inoculation temperature of 43° C. +/-2° and inoculated with 0.02% culture (Yo-Fa.st 16 Yogurt Culture, available from Chr. Hansen Holdings AIS, Hørsholm, Denmark,). The inoculated mixture was incubated for 3 to 4 hours at 43° C. to reach a target pH of 4.6. The mixture was then pumped using a stator pump through a #60 mesh screen and cooling system of the Model 25-2S processing equipment. Samples of the finished yogurt was collected in 4 oz. cups and cooled to 4° C., and evaluated.

1d. Viscosity Measurements

The viscosity of stirred yogurt samples prepared in accordance with Example 1c was measured using a Brookfield Model DV-II+ Viscometer (available from Brookfield Engineering Laboratories. Inc., Middleboro, Mass., USA) with a small sample adaptor and the following parameters:

Spindle #28, 30 RPM, 20 seconds, 12 g sample—output in centipoise (cP); and

Samples were at a temperature of approximately 4° C.

1e. Gel Strength Measurements

The gel strength of stirred yogurt samples prepared in accordance with Example 1c was measured using a Texture Analyzer, Model TA.XT2 (available from Texture Technologies Corp., Hamilton, Mass., USA) as follows. The yogurt peak gel strength was tested at approximately 4° C. In the 4 ounce cups in which the yogurt was collected. The reading was taken using a 1 inch acrylic cylinder at absolute peak force achieved during the 15 mm plunge into the sample. The probe moved through the sample at 0.2 mm/s.

1f. Yogurt Opacity Measurements

The opacity of stirred yogurt samples prepared in accordance with Example 1c was measured using an Evolution™ 60S UV-Visible Spectrophotometer with VISIONlite™ ColorCalc software (available from ThermoFisher Scientific. Inc., Waltham, Mass., USA) as follows. Yogurt was removed from the refrigerator and gently stirred with a plastic pipette. The pipette was used to load a small amount of yogurt into the 0.2 mm O-demountable quartz cuvette with removable window slide, making sure that the removable slide was tightly aligned with the window and air bubbles or voids avoided in the cuvette. The equipment was set for absorbance measurement mode (open Opacity method) and a white tile placed on the top to make a baseline for calibration. The yogurt-filled cuvette was then loaded after the calibration was completed, and the absorbance of light measured over 350-800 nm wavelength through the cuvette. Light absorbance (A) at 450 nm from the curve was recorded and used to represent opacity.

1g. Starch Materials

The inhibited starch ("IS") used in the Examples below is a hydroxypropyl stabilized, distarch phosphate, waxy maize starch stabilized with 6.6 wt. % propylene oxide and cross-linked with 0.036 wt. % phosphorus oxychloride. The non-granular, enzymatically-debranched waxy potato ("EDWP") starches used in the Examples below were prepared as described above in 1a using, the debranching times and enzyme dosages set forth in Table 1.

TABLE 1

EDWP Starches

| EDWP Starch | Enzyme Dosage (wt. %) | Debranching Time (hours) | Dextrose Equivalent (DE) |
|---|---|---|---|
| 1 | 0.15 | 10 | 3.8 |
| 2 | 0.15 | 15 | 3.7 |
| 3 | 0.15 | 20 | 3.9 |
| 4 | 0.25 | 10 | 4.5 |
| 5 | 0.25 | 15 | 4.1 |
| 6 | 0.25 | 20 | 5.0 |
| 7 | 0.37 | 10 | 5.1 |
| 8 | 0.37 | 15 | 5.0 |
| 9 | 0.37 | 20 | 6.7 |
| 10 | 0.50 | 10 | 4.6 |
| 11 | 0.50 | 15 | 4.6 |
| 12 | 0.50 | 20 | 5.5 |
| 13* | 0.25 | 15 | 3.0 |
| 14* | 0.50 | 15 | 3.9 |
| 15* | 0.50 | 3.5 | 3.7 |

*For starches 13-15, the starch dispersion was at 20-25% starch solids by weight during enzymatic debranching.

The comparative starch materials ("SM") used in the Examples are described in Table 2.

TABLE 2

Other Starch Materials

| SM No. | Description |
|---|---|
| SM 1 | Maltodextrin |
| SM 2 | Potato-based maltodextrin |
| SM 3 | Amylomaltase (4-α-glucanotransferase) modified potato starch |
| SM 4 | Starch blend containing granular thermally inhibited starch |

SM 1 = N-DULGE ® SA1 maltodextrin, available from Ingredion Incorporated, Bridgewater, New Jersey,
SM 2 = PASELLI ™ WFR maltodextrin, available from Avebe, Veendam, The Netherlands.
SM 3 = ETENIA ™ 457 potato starch, available from Avebe, Veendam, The Netherlands.
SM 4 = NOVATION ® Indulge 1720 functional native starch, available from Ingredion Incorporated, Bridgewater, New Jersey.

Example 2 and Comparative Examples A and B

Comparing the Performance of a Low Protein Yogurt Formulation Containing IS and EDWP Starches to a Full Protein Yogurt Formulation Only Containing IS Starch Yogurt formulations were produced according to the process described above in Example 1c using the formulae described in Table 3 below. The yogurt formulations described in Table 3 were evaluated for viscosity, gel strength and opacity, with the results of the evaluations set forth in Table 4 below.

TABLE 3

Yogurt Formulations

| | Examples | | |
|---|---|---|---|
| Ingredients (wt. %) | 2[1] | A[2] | B[3] |
| Water | 75.79 | 73.80 | 79.30 |
| Non-fat dry milk | 2.25 | 8.00 | 2.50 |
| IS | 3.00 | 2.00 | 2.00 |
| Heavy cream | 6.20 | 6.20 | 6.20 |
| Sugar | 10.00 | 10.00 | 10.00 |
| EDWP Starch No. 15 | 1.06 | 0 | 0 |
| Whey permeate[4] | 1.70 | 0 | 0 |
| Total | 100 | 100 | 100 |

[1]Low protein (1%) yogurt formulation containing a texturizing agent described herein.
[2]Full protein (2.9%) yogurt formulation.
[3]Low protein (1%) yogurt formulation with no texturizing agent described herein added thereto.
[4]Lactowell ® Whey Permeate, available from Lactalis Ingredients, Bourgbarré, France.

TABLE 4

Results of Yogurt Formulation Evaluations

| | Examples | | |
|---|---|---|---|
| Evaluation | 2 | A | B |
| Viscosity, cP (@ 7 days) | 6074 | 6041 | 500 |
| Gel strength, g (@ 7 days) | 25.58 | 27.6 | 11.66 |
| Opacity | 0.7440 | 0.8605 | 0.5925 |

Based on the above results, a low protein yogurt formulation (about 1% protein) containing the texturizing agent described herein (Ex. 2) has a comparable viscosity, gel strength and opacity to a full protein yogurt formulation control. (Ex. A) that does not contain the texturizing agent described herein.

Examples 3-13

Gel Strength Evaluation of Low Protein Yogurt Formulations Containing IS starch and Different EDWP Starches Twelve different low protein yogurt formulations (Examples 3-14) having about 2% protein were prepared according to the process described above and using the formula described in Table 5 below. Each of the twelve low-protein yogurt formulations that were evaluated contained a different EDWP starch set forth in Table 1. The Gel Strength Performance of each of the Ex. 3-14 yogurt formulations is set forth in Table 6 along with the Table 1 EDWP starch contained in each exemplary yogurt formulation and the DE associated therewith.

TABLE 5

Yogurt Formulation

| Ingredients | Amount (wt %) |
|---|---|
| Water | 81.80 |
| Non-fat dry milk | 5.50 |
| IS | 2.00 |
| Heavy Cream | 3.70 |
| Sugar | 5.00 |
| EDWP Starch from Table 1 | 2.00 |
| Total | 100.00 |

TABLE 6

Gel Strength of Ex 3-14 Yogurt Formulations

| Example | Table 1 EDWP Starch | DE of Table 1 EDWP Starch | Gel strength[1] (g) @ 7 days | Gel strength[1] (g) @ 7 weeks |
|---|---|---|---|---|
| 3 | 1 | 3.8 | 33.87 | 37.88 |
| 4 | 2 | 3.7 | 29.64 | 36.47 |
| 5 | 3 | 3.9 | 28.19 | 33.27 |
| 6 | 4 | 4.5 | 33.42 | 36.88 |
| 7 | 5 | 4.1 | 35.20 | 40.60 |
| 8 | 6 | 5.0 | 33.15 | 37.13 |
| 9 | 7 | 5.1 | 27.62 | 30.85 |
| 10 | 8 | 5.0 | 32.55 | 38.50 |
| 11 | 9 | 6.7 | 28.41 | 34.27 |
| 12 | 10 | 4.6 | 34.73 | 40.48 |
| 13 | 11 | 4.6 | 33.17 | 38.05 |
| 14 | 12 | 5.5 | 28.67 | 34.66 |

[1]Gel strength values are the average of two runs.

Based on the above results, yogurt formulations prepared with an EDWP starch having a DE of from about 3.8 to about 5 provided yogurts having the best gel strength.

Example 1.5 and Comparative Examples C-G

Comparing the Performance of Low Protein Yogurt Formulations Containing IS and EDWP Starches to Full and Low Protein Yogurt Formulations Containing an IS Starch Alone or in Combination with a Non-EDWP Starch Yogurt formulations according to the invention are compared to yogurt formulations prepared with commercially available starches. Example 15 (1% protein) and. Comparative Example C, D, E, and G (1% protein) and F (2.9% protein) yogurt formulations were produced according to the process described above using the formulae described in Table 7 below. The characteristics of the Ex. 15 and Comparative Ex. C, D, E, F, and G yogurt formulations are described in Table 8 below.

TABLE 7

Yogurt Formulations

| Ingredients (wt %) | Ex. 15 | Comparative Ex. C | Comparative Ex. D | Comparative Ex. E | Comparative Ex. F | Comparative Ex. G |
|---|---|---|---|---|---|---|
| Water | 80.98 | 80.97 | 80.97 | 80.91 | 77.40 | 82.80 |
| Non-fat dry milk | 2.70 | 2.70 | 2.70 | 2.70 | 8.10 | 2.70 |
| IS | 2.00 | 2.00 | 2.00 | 2.00 | 2.00 | 2.00 |
| Heavy cream | 2.50 | 2.50 | 2.50 | 2.50 | 2.50 | 2.50 |
| Sugar | 10.00 | 10.00 | 10.00 | 10.00 | 10.00 | 10.00 |
| EDWP Starch 13 | 1.82 | 0.00 | 0.00 | 0.00 | 0.00 | 0.00 |
| SM 1 | 0.00 | 1.83 | 0.00 | 0.00 | 0.00 | 0.00 |
| SM 2 | 0.00 | 0.00 | 1.83 | 0.00 | 0.00 | 0.00 |
| SM 3 | 1.00 | 0.00 | 0.00 | 1.89 | 0.00 | 0.00 |
| Total | 100 | 100 | 100 | 100 | 100 | 100 |

TABLE 8

Characteristics of Ex. 15 and Comparative Ex. C-G Yogurt Formulations

| Yogurt Formulation | Gel strength (g) @ 7 days | Opacity (A) |
|---|---|---|
| 15 | 23.90 | 0.695 |
| C | 12.42 | 0.642 |
| D | 17.86 | 0.700 |
| E | 32.92 | 0.557 |
| F | 21.50 | 0.790 |
| G | 11.06 | 0.505 |

The above Table 8 results show that a low protein yogurt formulation containing a texturizing agent described herein (Ex.15) provides viscosity, gel strength and opacity that is comparable or equivalent to a full protein yogurt formulation(Ex. F). In contrast, the low protein yogurt formulations of Comparative Exs. C, D, and E did not have an opacity and gel strength that were comparable or equivalent to the full protein yogurt formulation of Ex. F.

Example 16 and Comparative Examples H and I

Comparing the Performance of a Low Protein Yogurt Formulations Containing IS and EDW P Starches to Full and Low Protein Yogurt Formulations Containing IS Starch Alone The yogurt formulations of Example 16 (at 1% protein) and Comparative Examples H and I (at 2.9% and 1% protein, respectively) were produced according to the process described above and using the formulae described in Table 9 below.The characteristics of these yogurt formulations are described in Table 10 below. The Ex. 16 and Comparative Ex, I yogurt formulations were low protein (1% protein) formulations, and Comparative Ex H was a full protein (2.9% protein) yogurt formulation.

TABLE 9

Yogurt Formulations

| Ingredients (wt %) | Ex 16 (1% protein) | Comparative Ex. H (2.9% protein) | Comparative Ex. I (1% protein) |
|---|---|---|---|
| Water | 83.15 | 79.70 | 85.15 |
| Non-fat dry milk | 2.85 | 8.30 | 2.85 |

TABLE 9-continued

Yogurt Formulations

| Ingredients (wt %) | Ex 16 (1% protein) | Comparative Ex. H (2.9% protein) | Comparative Ex. I (1% protein) |
|---|---|---|---|
| IS | 2.00 | 2.00 | 2.00 |
| Sugar | 10.00 | 10.00 | 10.00 |
| EDWP Starch 14 | 2.00 | 0.00 | 0.00 |
| Total | 100.00 | 100.00 | 100.00 |

TABLE 10

Characteristics of Ex. 16 and Comparative Ex. H and I Yogurt Formulations

| Yogurt Formulation | Viscosity (cP) @ 7 days | Gel strength (g) @ 7 days | Opacity (A) |
|---|---|---|---|
| 16 | 4083 | 20.93 | 0.550 |
| H | 4333 | 21.30 | 0.733 |
| I | 183 | 11.1 | 0.323 |

The above Table 10 results show that a low protein yogurt formulation containing a texturizing agent described herein (Ex. 16, 1% protein) has a viscosity, gel strength and opacity comparable or equivalent to a full protein yogurt formulation control (Ex. H).

The above description is for the purpose of teaching the person of ordinary skill in the art how to practice the invention, and it is not intended to detail all those obvious modifications and variations which will become apparent to the skilled worker upon reading the description. It is intended, however, that all such obvious modifications and variations be included within the scope of the invention defined by the following claims.

What is claimed is:

1. A low protein yogurt composition comprising:
   a. at least one dairy ingredient, dairy alternative ingredient, or mixture thereof; and
   b. a texturizing agent comprising an inhibited starch and a non-granular, enzymatically-debranched waxy potato starch,
   wherein said low protein yogurt composition comprises less than 2.9% dairy protein content by weight of said composition.

2. The composition of claim 1, wherein said composition comprises an effective amount of said texturizing agent to thicken, gel, or thicken and gel the low protein yogurt composition.

3. The composition of claim 1, wherein said composition further comprises water.

4. The composition of claim 1, wherein said composition further comprises a viscosity of at least about 4000 centipoise, and wherein said texturizing agent is a viscosifier and said composition comprises an effective amount of the texturizing agent to provide the viscosity.

5. The composition according to claim 4, wherein said viscosity is measured according to a viscosity measurement test at 4°C.

6. The composition of claim 1, wherein said composition further comprises a gel strength of at least about 13 grams, from about 13 grams to about 400 grams, from about 13 grams to about 200 grams, from about 13 grams to about 100 grams, from about 15 grams to about 50 grams, from about 20 grams to about 45 grams, from about 22 grams to about 45 grams, or from about 25 grams to about 42 grams; and wherein said composition comprises an effective amount of said texturizing agent to provide said gel strength.

7. The composition of claim 6, wherein the gel strength is measured according to a gel strength measurement test at 4°C.

8. The composition of claim 1, wherein said composition further comprises an opacity of at least about 0.500 A, from about 0.500 A to about 0.850 A, or from about 0.550 A to about 0.800 A, wherein said composition comprises an effective amount of said texturizing agent to provide said opacity.

9. The composition of claim 8, wherein the opacity is measured according to the yogurt opacity measurement test after refrigeration of the composition.

10. The composition of claim 1, wherein said composition comprises a dairy protein content of less than or equal to about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, or 2.8% by weight of the composition.

11. The composition of claim 1, wherein the inhibited starch and non-granular, enzymatically-debranched waxy potato starch are present in the texturizing agent in a weight ratio of at least 1.0:1.0, about 3.0:1.0, or about 1.0:1.0 to about 4.0:1.0.

12. The composition of claim 1, wherein the non-granular, enzymatically-debranched waxy potato starch has a dextrose equivalent of about 10.0 or less, from about 2.0 to about 9.0, from about 2.5 to about 8.0, from about 3.0 to about 7.0, from about 3.5 to about 5.0, or from about 4.0 to about 5.0.

13. The composition of claim 1, wherein said composition comprises the texturizing agent in an amount of about 10.0% or less, about 0.5% to about 10%, about 0.5% to about 8.0%, about 1.5% to about 7.0%, about 2.0% to about 6.0%, or about 3.0% to about 5.0%, by weight of the composition.

14. The composition of claim 1, wherein the texturizing agent is the sole texturizing agent in the composition.

15. The composition of claim 1, with the proviso that said composition does not contain at least one other texturizing agent or with the proviso that said texturizing agent is the sole texturizing agent in the composition.

16. The composition of claim 1, wherein the non-granular, enzymatically-debranched waxy potato starch is debranched with an α-1,6-D-glucanohydrolase.

17. The composition of claim 16, wherein the α-1,6-D-glucanohydrolase is an isoamylase, pullulanase, or combination thereof.

18. The composition of claim 1, wherein the non-granular, enzymatically-debranched waxy potato starch is partially debranched.

19. A method of making a low protein yogurt composition comprising less than 2.9% dairy protein content by weight of said composition, wherein said method comprises:
   a. mixing together at least one dairy or alternative dairy ingredient, a texturizing agent comprising an inhibited starch and a non-granular, enzymatically-debranched waxy potato starch, and, optionally, water, to form a yogurt base, and
   b. culturing the yogurt base,
   wherein said texturizing agent is present in an effective amount to thicken, gel, or thicken and gel the low protein yogurt composition.

20. A low protein yogurt composition containing a texturizing agent comprising an inhibited starch and a non-granular, enzymatically-debranched waxy potato starch, wherein the weight ratio of the inhibited starch to the non-granular, enzymatically-debranched waxy potato starch is at least 1.0:1.0, about 3.0:1.0, or from about 1.0:1.0 to about 4.0:1.0, and wherein the non-granular, enzymatically-debranched waxy potato starch has a dextrose equivalent of about 10.0 or less, from about 2.0 to about 9.0, from about 2.5 to about 8.0, from about 3.0 to about 7.0, from about 3.5 to about 5.0, or from about 4.0 to about 5.0wherein said texturing agent is present in an effective amount to thicken, gel or thicken and gel, the low protein yogurt composition, and the composition comprises less than 2.9 % dairy protein content by weight of said composition.

* * * * *